United States Patent [19]

Mori

[11] Patent Number: 4,524,758
[45] Date of Patent: Jun. 25, 1985

[54] SOLAR RAY COLLECTING DEVICE

[76] Inventor: Kei Mori, 3-16-3-501, Kaminoge, Setagaya-ku, Tokyo, Japan

[21] Appl. No.: 620,405

[22] Filed: Jun. 14, 1984

[30] Foreign Application Priority Data

Jun. 24, 1983 [JP] Japan ................................ 58-114766

[51] Int. Cl.³ ............................................... F24J 3/02
[52] U.S. Cl. .................................... 126/440; 126/424; 126/443
[58] Field of Search ................ 126/438, 439, 440, 424, 126/425, 443

[56] References Cited

U.S. PATENT DOCUMENTS

| | | | |
|---|---|---|---|
| 497,079 | 5/1893 | Severy | 126/424 |
| 4,175,540 | 11/1979 | Roantree et al. | 126/425 |
| 4,461,278 | 7/1984 | Mori | 126/440 |

FOREIGN PATENT DOCUMENTS 68750 6/1981 Japan .................................. 126/440

Primary Examiner—James C. Yeung
Attorney, Agent, or Firm—Jordan and Hamburg

[57] ABSTRACT

A solar ray collecting device which can be preferably used at a place near the North Pole or South Pole comprises a supporting post capable of moving rotatably, a rotatable shaft crossing perpendicularly to said supporting shaft at the top portion thereof, and a large number of solar ray collecting elements, each solar ray collecting element being rotatably installed around the shaft perpendicular to the rotatable shaft. Each of the solar ray collecting elements comprises a large number of lenses, an optical conductor having a light-receiving edge positioned at the focus of said respective lenses, and a transparent cover for covering the surface the lenses.

A larger number of the lenses are arranged along a vertical direction rather than a horizontal direction. The cover is formed in the shape of a circular arc to the horizontal direction and is in the shape of a straight line to the vertical direction.

10 Claims, 5 Drawing Figures

SOLAR RAY COLLECTING DEVICE

BACKGROUND OF THE INVENTION

The present invention relates to a solar ray collecting device, particularly a solar ray collecting device which can be preferably used at a place near the North Pole or South Pole.

It has been already proposed that a solar ray is focused by a lens, etc. and guided into an optical conductor cable, and further guided to an optional desired place for instance, the place to be illuminated for the purpose of illuminating the place. On that occasion, in order to effectively guide the solar ray into the optical conductor cable, the direction of the sun is detected by a solar ray direction sensor, etc. and the surface of the lens is so controlled as to always face towards the sun. One of such methods is to focus the solar ray by means of the Fresnel lens of about 40 cm diameter to guide the solar ray focussed by the lens into the light conductor having an edge surface of about 10 mm diameter arranged at the focus position of the lens, and to transmit the solar ray guided into the light conductor in such a manner through the light conductor to the optional desired position in order to use the solar ray for illumination or other purposes, for instance, as the light source for cultivating the plants in a room or an underground room, the light source for nurturing plants on the bottom of the sea, or the light source for culturing chlorella, etc. However, according to such method, the focal distance of the lens turns out to be longer, for instance, about 40 cm, and therefore the device becomes large-scaled or voluminous. And furthter, the light collecting energy per lens increases so that highly heat-proof material needs to be used as the member placed near to the focus position of the lens, and the operator may probably be in danger of suffering from burning the operator's hands, etc. at the focus position when the operator performs adjustment work for positioning the edge surface of the light conductor onto the focus position of the lens, and so on. According to the method, a large number of small lenses having a diameter of about 4 cm is used, and the edge surface of the optical fiber of 1 through 2 mm diameter is arranged at the focus position of each lens. The light collected by each lens is guided into the respective optical fibers, and the lights delivered from the respective optical fibers are guided into the optical conductor having a large diameter, for instance a diameter of 10 through 30 mm and transmitted to the optional desired position through the light conductor.

According to this method mentioned above, the focal distance of the lens turns out to be small, for instance, about 4 cm. Therefore, it may be possible to realize the device manufactured in a small-scaled and thin style. On the contrary, since a large number of lenses in used, it may be troublesome to position the light-receiving edge surface of the optical fiber onto the focus of each lens and perform its maintenance work.

The afore-mentioned solar ray collecting devices are constructed for possible widespread use on earth. Therefore the device needs a globular capsule and a gathered lens-assembly is constructed so as to form the outer circumferential surface approximately in the shape of a circle entirely corresponding to the shape of the capsule. However, considering that the afore-mentioned solar ray collecting device is used only at predetermined locations on earth, it may be possible to construct the device more effectively depending on the location. For instance, considering that the device is used at a place near the North Pole or South Pole, the sun moves along in an approximate horizontal, circular line from the east to the south, the west, and the north, so that the movement of the sun hardly shows the height variation along with a direction from the south to the north. Therefore, the capsule does not need to be formed in the shape of a globe. Furthermore, even though the surface of the capsule is perpendicular to the light progressing along a horizontal direction, the solar ray is not reflected on the surface of the capsule but it can be guided into the capsule.

SUMMARY OF THE INVENTION

The primary object of the present invention is to provide a solar ray collecting device which can be preferably used at a place near the poles.

The solar ray collecting device comprises a supporting post capable of moving rotatably, a rotatable shaft crossing perpendicularly to the supporting shaft at the top portion thereof, and a large number of solar ray collecting elements, each solar ray collecting element being rotatably installed around the shaft perpendicular to the rotatable shaft. Each of the solar ray collecting elements comprises a large number of lenses, an optical conductor having a light-receiving edge positioned at the focus said respective lenses, and a transparent cover for covering the surface the lenses. A larger number of the lenses are arranged along a vertical direction rather than a horizontal direction, and the cover is formed in the shape of a circular arc to the horizontal direction and is in the shape of a straight line to the vertical direction.

The above and other objects, features and advantages of the present invention will become apparent from the following detailed description taken with the accompanying drawings.

DESCRIPTION OF THE PREFERRED EMBODIMENTS

Figure 1:
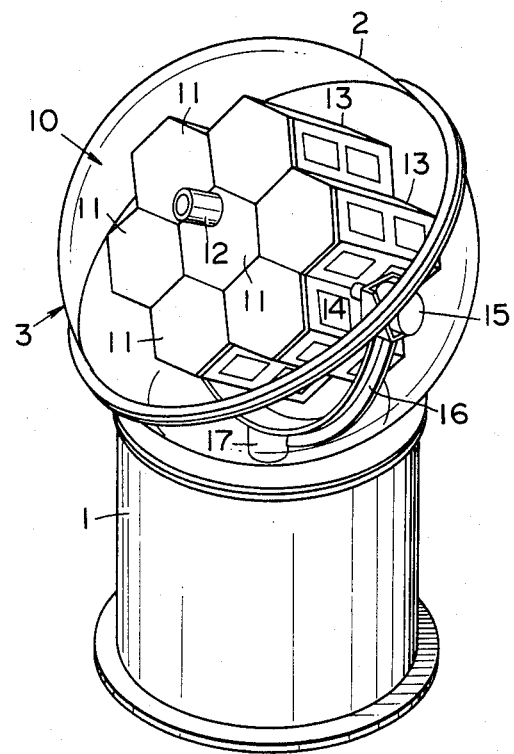
FIG. 1 shows entirely an embodiment of a conventional solar ray collecting device.

FIG. 1 is a perspective view showing entirely an embodiment of the solar ray collecting device previously proposed by the present applicant. In FIG. 1, 1 is a cylindrical basic portion, and 2 is a transparent dome-shaped head portion. A capsule 3 for the solar ray collecting device is constructed with the basic portion 1 and the head portion 2. When the device is used, a solar ray collecting device 10 is accommodated in the capsule 3 as shown in FIG. 1.

The solar ray collecting device 10 comprises a large number of (for instance, 7 or 19) lenses 11, a solar ray direction sensor 12 for detecting the direction of the sun, supporting frames 13 for unitarily supporting the lenses 11 and the sensor 12, a first rotatable shaft 14 for rotatably moving the supporting frame 13, a first motor 15 for rotating the first rotatable shaft 14, a supporting arm 16 for supporting the lenses 11, the sensor 12, the frame 13, the shaft 14, and the motor 15, a second rotatable shaft 17, installed perpendicularly to the first rotatable shaft 14, and a second motor (not shown in the drawing). The solar ray direction sensor 12 detects the direction of the sun and produces a detection signal which controls the first and second motors so as to always direct the lenses 11 to the direction of the sun. And then, the solar ray is guided into the optical conductor cable, the light-receiving edge of which is located at the focus of the lens 11, and the solar ray is further transmitted to an optional desired place through the optical conductor cable.

The afore-mentioned solar ray collecting device is constructed for possible widespread use on planet earth. Therefore the device needs a globular capsule and a gathered lens-assembly is constructed so as to form the outer circumferential surface approximately in the shape of a circle entirely corresponding to the shape of the capsule. However, considering that the afore-mentioned solar ray collecting device is used only at predetermined locations on earth, it may be possible to construct the device more effectively depending on the location. For instance, considering that the device is used at a place near the North Pole or South Pole, the sun moves along in an approximate horizontal, circular line from the east to the south, the west, and the north, so that the movement of the sun hardly shows the height variation along with a direction from the south to the north. Therefore, the capsule does not need to be formed in the shape of a globe. Furthermore, even though the surface of the capsule is perpendicular to the light progressing along a horizontal direction, the solar ray is not reflected on the surface of the capsule but it can be guided into the capsule.

Figure 2:
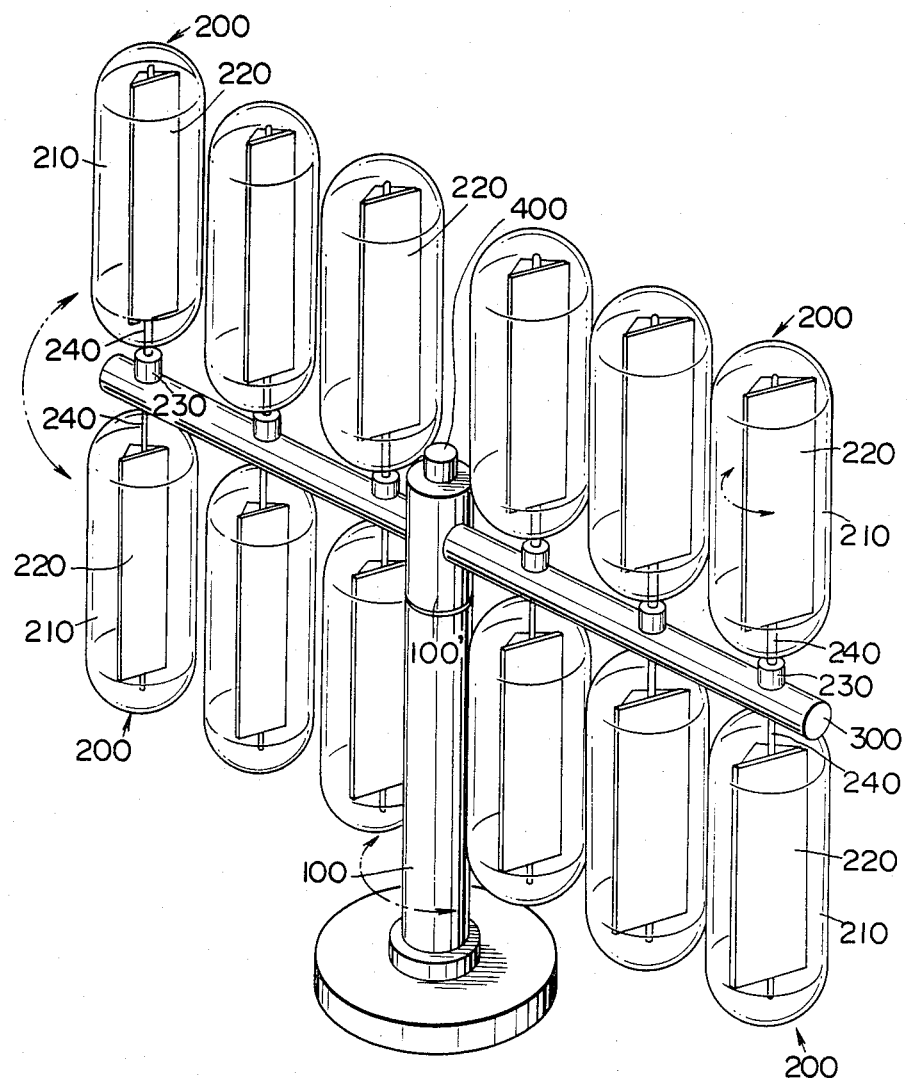
FIGS. 2 through 5 illustrate an embodiment of the solar ray collecting device according to the present invention.
Figure 3:
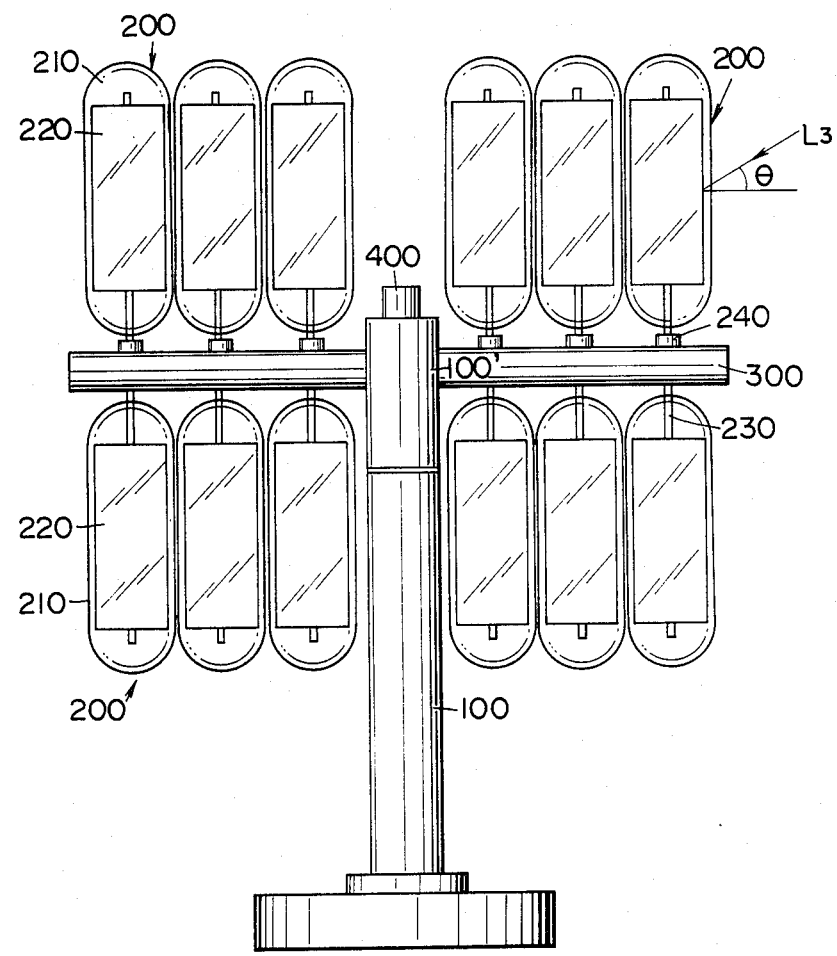

FIGS. 2 through 5 illustrate an embodiment of the solar ray collecting device according to the present invention. FIG. 2 is a perspective view for explaining an embodiment of a solar ray collecting device according to the present invention. FIG. 3 a front view, FIG. 4 a plane view, and FIG. 5 a cross-sectional view in explanation of a main portion of the solar ray collecting device. Among the figures, 100 is a rotatable supporting post; 200 are solar ray collecting portions; and 300 is a rotatable shaft for supporting a large number of solar ray collecting elements. The respective solar ray collecting portions 200 comprises a capsule 210 and a light collecting element 220 comprising of a large number of lenses installed in the capsule and optical conductors having respectively a light-receiving edge located at the focus of the lens. The light collecting elements 220 are moved rotatably around the shaft 240 and elongated up and down by the motor 230, respectively. Describing in more detail, the light collecting elements 220 are so controlled by the motor 230 as to direct the lens surface thereof to the east in the morning, to the south at noon, to the west in the evening, and to the north at midnight.

The lens used in the present invention is 4 cm or less in its diameter, and a large number of lenses (for instance, about 2000 lenses) are used per one light collection portion. The light-receiving edge of the optical fiber is about 0.1 to 0.2 mm in its diameter and it is precisely positioned at the focus of the respective lenses. The solar ray focused by the lens is guided into the respective optical fibers. In such a manner, the lens of a small diameter enables it to shorten the focal distance thereof. It follows that a very thin solar ray collecting element can be constructed. The respective optical fibers are installed through the rotatable shaft 240, the rotatable shaft 300, and the rotatable supporting post 100. As mentioned before, the solar rays guided into the optical fibers are further transmitted to the optional desired place through the optical fibers and used for the desired purpose.

As mentioned so far, the solar ray collecting device according to the present invention is used at the place near the poles. Taking the case of the North Pole as an example, when the sun is nearly located at the place above the tropic of Cancer around the earth, the sun radiates its solar rays onto the North Pole throughout the day during the summer season. Namely, the sun progresses from the east to the south, the west, and the north in horizontal fashion.

Figure 4:
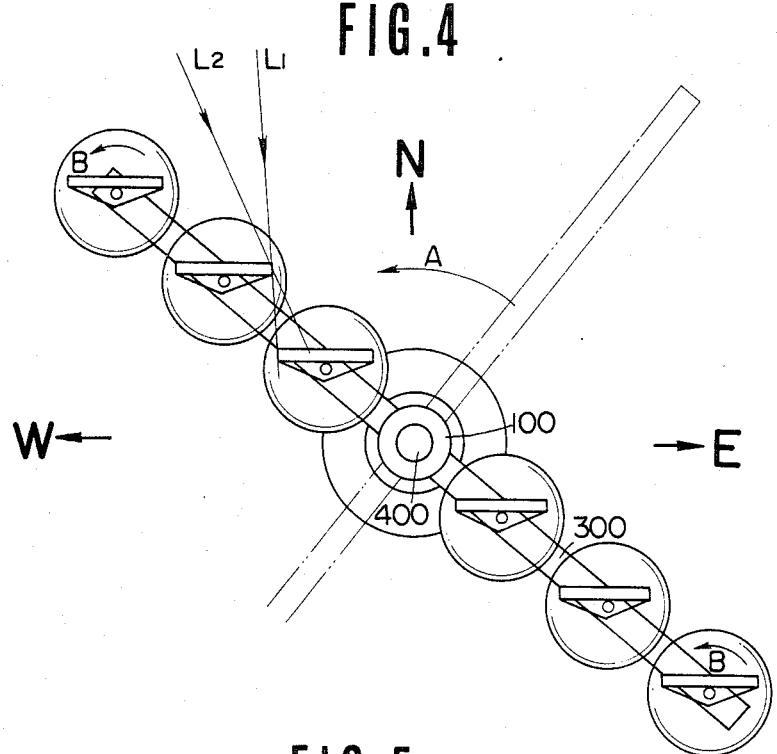

When the sun progresses from the east to the south, the motor 230 rotates the rotatable shaft 240 to control the light-receiving surface of the light collecting element 220 so as to direct it towards the sun. At noon, the light-receiving surface thereof is directed due south as shown in FIG. 4.

Afterwards, the sun further progresses from the south to the west and the light-receiving surface of the light collecting element 220 is rotated around the rotatable shaft 240 to the direction of an arrow B following the movement of the sun. During the afore-mentioned time interval, the solar rays come from the direction shown by $L_1$. And later, when they come from the direction shown by $L_2$, the west-side solar ray collecting elements project shadows towards the east-side solar ray collecting elements so that the solar rays do not arrive at the east-side solar ray collecting elements. The rotatable shaft 100 is so constructed as to move rotatably in order to avoid such inconvenience. At a later time than noon, the rotatable shaft 100 is rotated by the motor 110 to the direction of arrow A so that the entire rotatable shaft 300 is rotated thereby and situated at the position shown by a dots-and-dash line as shown in FIG. 4. Since then, it may be possible to collect the solar rays without any inconvenience as mentioned before until the sun progresses to the west. During this time interval, the solar ray collecting element 220 rotates by 180° following the movement of the sun and the rotatable supporting post 100 also rotates by 90° at the same time. Therefore, the relative rotation angle between the solar ray collecting element 220 and the rotatable shaft 300 turns out to be 90°.

Afterwards, the sun further progresses from the west to the north. During this time interval, the front solar ray collecting elements project shadows toward the near solar ray collecting elements as mentioned before. Therefore, it may be necessary to do same adjustment as mentioned before, when the sun progresses a little to the north from the due west. At this time, the rotatable shaft 100 is also rotated by 90°. In consequence, the relative rotation angle turns out to be 90° at maximum.

And further, when the sun progresses from the north to the east, it may be necessary to do same adjustment as mentioned before. At this time, the rotatable supporting post 100 is turned back by 90°. And further, when the sun arrived at the due east the post 100 is also turned back by 90° in order to put it back in the intial condition as shown in FIG. 4. Consequently, the maximum relative rotation angle between the solar ray collecting element 220 and the rotatable shaft 300 turns out to be 180°. And the rotation angle of the rotatable supporting post also turns out to be 180° at maximum. On such condition, it may be possible to decrease twisting of the optical fiber and easily guide the optical fiber outside.

The case of using the solar ray collecting device according to the present invention at the North Pole zone is described heretofore. However, it may be also possible to use such device in the South Pole zone as a matter of course. On the latter occasion, the rotating direction of the rotatable supporting post 100 needs to be reversed. And then, the variation of the sun's height and its direction is not so large at the North Pole zone or at the South Pole zone. In consequence, even though the surface of the capsule 210 is formed in the shape of vertically straight line, the solar ray is easily guided into the capsule. To state more definitely, though the incidence angle $\theta$ at which the light $L_3$ is guided into the capsule differs from another according to the quality of the material (the refractive index thereof), the solar ray can be easily guided into the capsule without any trouble in the range of 45° or less (incidence angle $\theta$). Therefore, the capsule 210 can be constructed in the shape of a cylinder elongated vertically as shown in FIGS. 2 and 3. It may be possible to realize an arrangement construction of the solar ray collecting elements as shown in those figures by use of such assembly as mentioned so far.

However, on such occasion, the light-receiving surface of the solar ray collecting element 220 needs to be always directed toward the sun. If it is not directed toward the sun, the focal point of the solar ray focused by the lens does not coincide with the light-receiving surface of the optical fiber. Therefore, it follows that the solar ray can not be effectively guided into the optical fiber.

Figure 5:
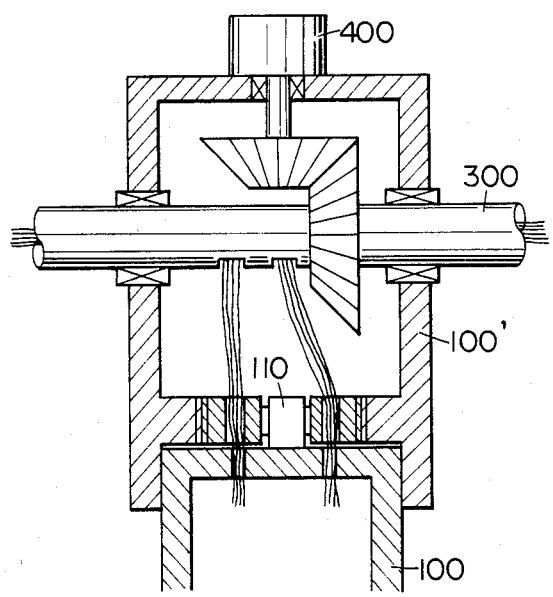

In order to settle such troublesome problems, the rotatable shaft 300 is so constructed as to move rotatably and it is rotated by a motor 400 installed on the rotatable supporting post 100' as shown in FIG. 5. Moreover, though the rotatable supporting post 100' is installed on the supporting post 100 and only the post 100' is rotated by the motor 400 in the case of construction shown in FIG. 5, it will be easily understood that the post 100 and the other post 100' may be unitarily combined and rotated entirely, as a matter of course.

As is apparent from the foregoing description, it may be possible to provide a preferable solar ray collecting device which can be used in the North Pole zone and the South Pole zone.

What is claimed is:

1. A solar ray collecting device for collecting solar rays from the sun, comprising a rotatable support post having a generally vertical axis, a support post motor for rotating said support post about said vertical axis, a rod having a rod axis disposed generally perpendicular to the vertical axis of said support post, said rod having a longitudinal central portion mounted on said support post such that said rod rotates in a generally horizontal plane as said support post motor rotates said support post, a plurality of solar ray collecting elements each rotatable about a generally upright shaft, each of said collecting elements having a drive means for rotating the respective collecting element about the axis of its upright shaft, said plurality of drive means being carried by said rod and being longitudinally spaced along the longitudinal length of said rod, each of said collecting elements including a plurality of light collecting lens means and optical conductors having a light-receiving edge located at the focus of said lens means, each of said upright shafts along with said rod and said support post having hollow portions, said conductors passing from said light-receiving edge through the hollow portions of the respective upright shaft, said rod and said support post, whereby each of said drive means is operable to rotate its respective collecting element alternately in both directions while said support post motor rotates said support post alternately in both directions in a manner to preclude the shadow of one collecting element impinging on the lens means on another collecting element as the sun traverses a 360 degree path about the solar ray collecting device while also limiting the maximum twist imparted to said conductors passing through said hollow portions of said upright shaft, said rod and said support post.

2. A device according to claim 1, wherein each of said drive means comprises a drive motor.

3. A device according to claim 1, wherein each of said drive means rotates its respective collecting element a maximum of 180 degrees.

4. A device according to claim 1, wherein said support motor rotates said support post a maximum of 180 degrees.

5. A device according to claim 1, wherein each of said solar ray collecting elements comprises a transparent cover in which said lens means are disposed, said optical conductors having the light-receiving edges thereof located at the focus of said lens means.

6. A device according to claim 1 further comprising a rod motor on said support post for rotating said rod about said rod axis.

7. A device according to claim 1 wherein a plurality of said collecting elements are disposed in a position above said rod, and another plurality of said collecting elements are disposed in a position below said rod.

8. A device according to claim 1, wherein each of said upright shafts is perpendicular to the axis of said rod.

9. A device according to claim 1, wherein each of said upright shafts is vertically disposed.

10. A solar ray collecting device for collecting solar rays from the sun, comprising a rotatable support post having a generally vertical axis, a support post motor for rotating said support post about said vertical axis, a rod having a rod axis disposed generally perpendicular to the vertical axis of said support post, said rod having a longitudinal central portion mounted on said support post such that said rod rotates in a generally horizontal plane as said support post motor rotates said support post, a plurality of solar ray collecting elements each rotatable about a generally upright shaft, each of said collecting elements having a collecting element motor for rotating the respective collecting element about the axis of its upright shaft, said collecting element motors being carried by said rod and being longitudinally spaced along the longitudinal length of said rod, each of said collecting elements including a plurality of light-collecting lens means and optical conductors having a light-receiving edge located at the focus of said lens means, each of said upright shafts along with said rod and said support post having hollow portions, said conductors passing from said light-receiving edge through the hollow portions of the respective upright shaft, said rod and said support post, whereby each of said collecting element motors is operable to rotate its respective collecting element through 180 degrees in both direction while said support post motor rotates said support post through 180 degrees in both directions in a manner to preclude the shadow of one collecting element impinging on the lens means on another collecting element as the sun traverses a 360 degree path about the solar ray collecting device while also limiting the maximum twist imparted to said conductors passing through said hollow portions of said upright shafts, said rod and said support post.

* * * * *